United States Patent [19]
Woog

[11] 3,966,359
[45] June 29, 1976

[54] APPARATUS FOR BODY HYGIENE

[75] Inventor: Philippe-Guy Woog, Geneva, Switzerland

[73] Assignee: Les Produits Associes, SA, Geneva, Switzerland

[22] Filed: Feb. 28, 1975

[21] Appl. No.: 554,175

[30] Foreign Application Priority Data
Mar. 1, 1974 Switzerland............ 2895/74

[52] U.S. Cl.................. 417/38; 417/415; 128/66; 417/440
[51] Int. Cl.² ............ F04B 49/02; F04B 49/08
[58] Field of Search ............ 417/36, 38, 415, 440; 128/66 R; 15/22

[56] References Cited
UNITED STATES PATENTS

| | | | |
|---|---|---|---|
| 3,578,884 | 5/1971 | Jocobson | 128/66 |
| 3,720,486 | 3/1973 | Jousson | 417/440 |
| 3,882,864 | 5/1975 | Montgomery | 128/66 |

Primary Examiner—William L. Freeh
Attorney, Agent, or Firm—Pennie & Edmonds

[57] ABSTRACT

Apparatus for body hygiene comprises an hydraulic pump and electric motor for producing liquid pressure pulses which are supplied to a hand appliance containing an hydraulic motor for driving a working tool, particularly a toothbrush, and means for alternatively supplying the pulses to a liquid jet attachment. The pump includes a pressure regulator. A control member coupled with the pressure regulator and an electric switch for the motor turn the motor on at maximum pressure of the liquid pulses.

9 Claims, 9 Drawing Figures

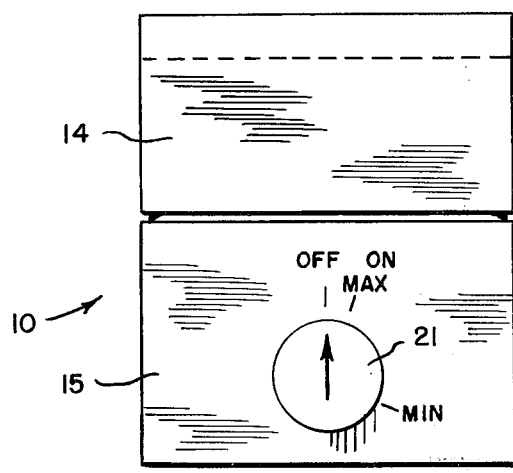
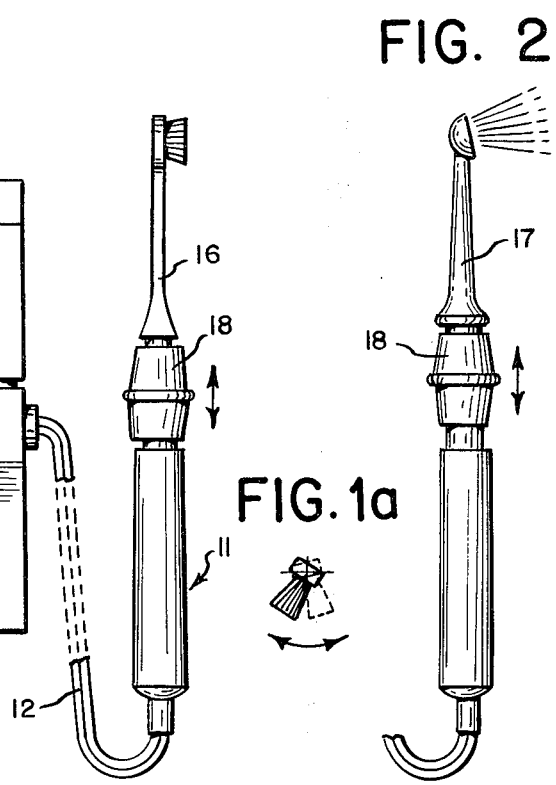
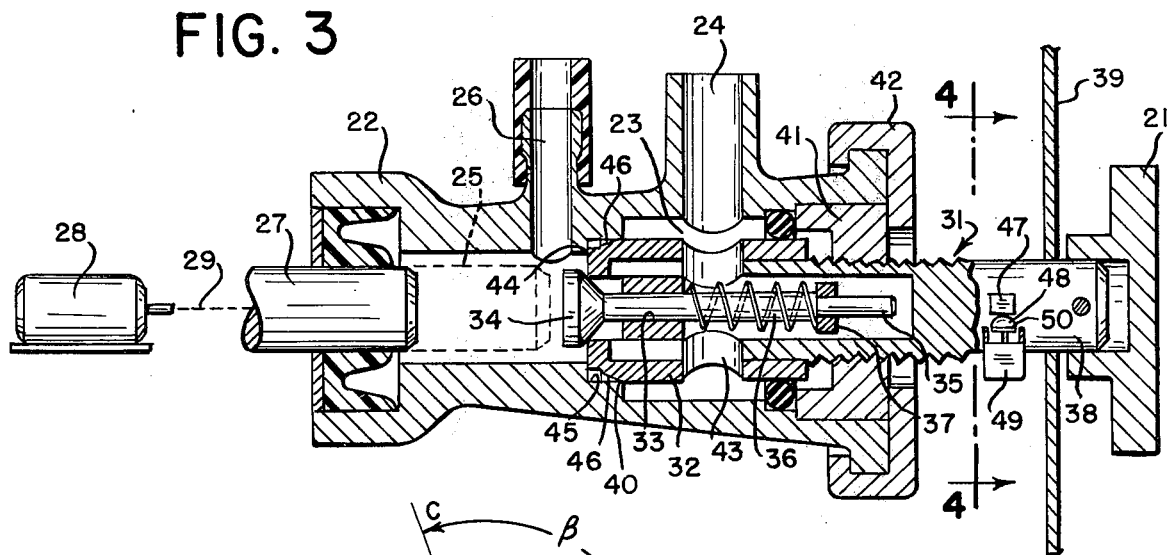
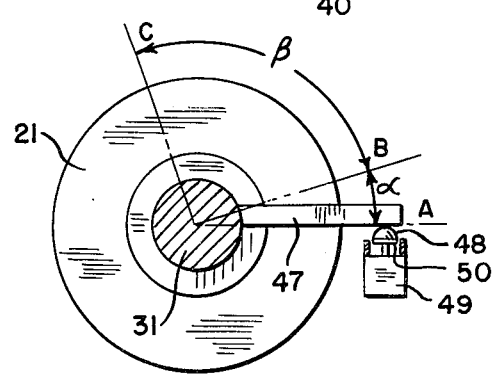

APPARATUS FOR BODY HYGIENE

The present invention relates to apparatus for body hygiene comprising an hydraulic pump driven by an electric motor for producing liquid pulses. The pulses are supplied to a hand appliance containing an hydraulic motor for oscillating a working too, particularly a toothbrush, or to a spray nozzle device, particularly for washing and massaging the buccal cavity. The hydraulic pump is provided with a regulating member movable between two extreme positions in order to vary the pressure of the liquid pressure pulses between a minimum value and a maximum value.

Such apparatus using, in particular, a hand appliance comprising a casing forming a handle in which there is mounted an hydraulic motor and a bypass system enabling the same hand appliance to be used alternately either to actuate a toothbrush or to feed a spray nozzle, is already known and comprises an electric switch for the control of the pump motor and an independent pressure-regulating knob.

On the other hand, spray devices are known in which provision is made for the pressure-regulating member to be coupled to the control switch of the pump motor in such a manner that the motor and the pump are stopped if this regulating member is in the minimum-pressure position and the motor is started when this member is displaced from its minimum position. Although, according to this last form of embodiment, a single manipulating member is provided, if it were desired to use this same device to actuate a toothbrush, there is the disadvantage that after the starting of the electric motor by the user, the pump is in the minimum-pressure position which is not sufficient to drive the hydraulic motor. Moreover, in the hydraulic systems mentioned, it is desirable, when starting the pump after a stoppage period of several hours or a few days, to have a maximum pressure in order to accelerate bringing the hydraulic circuit to its proper operating condition.

The user of a mouth-washing device serving both for the washing and for brushing the teeth, customarily begins his toilet by the brushing operation, which makes it necessary for the pressure of the pump to be maximum, which condition is not met with the devices hitherto known.

The object of the invention is to overcome these disadvantages and to create a device comprising a single operating member for the pump, the characteristic of which is well adapted to the needs of the device and requires minimum manipulation on the part of the user.

For this purpose, the apparatus according to the invention is characterized in that the electric switch of the electric motor is automatically brought into its open position by said pressure-regulating member when this member is in its extreme position corresponding to maximum pressure, and is closed when this member is displaced from said extreme position to a level of pressure passing from the maximum to the minimum.

By this means, allowance is made for the fact that this type of apparatus is used first for brushing the teeth and then for spraying, in such a manner that the user has only to displace the regulating member slightly to start the pump and this works with its maximum pressure necessary to drive the brush, and a possible additional manipulation of the member is only necessary when the toothbrush is replaced by the spray nozzle and it is desired to work with a spraying pressure lower than the maximum pressure.

The invention will be better understood from the following description of examples of embodiment with reference to the accompanying drawing, in which:

FIG. 1 illustrates the overall apparatus including the pump unit and hand appliance with a toothbrush attachment in place, and FIG. 1(a) illustrates rotational oscillation thereof;

FIG. 2 illustrates the hand appliance with a water jet attachment in place;

FIG. 3 is a longitudinal section of the pump and associated control means, taken through the pump regulating member;

FIG. 4 is a diagrammatic section on line 4—4 of FIG. 3, with the wall of the pump housing removed;

Figure 5:
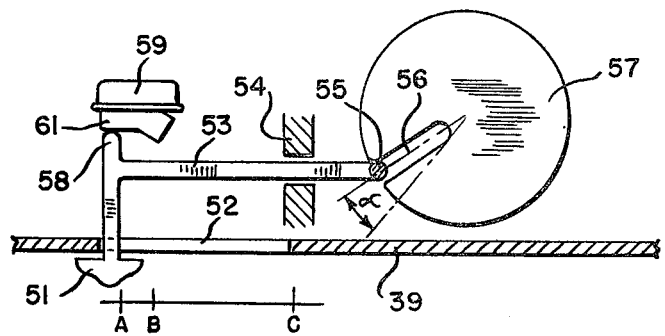
FIG. 5 is a diagrammatic longitudinal view, in section, of a modified embodiment of the regulating means in the stopped position.

Referring to FIG. 1, a pump unit generally designated as 10 is shown, connected to a hand appliance generally designated as 11 by a flexible tube 12. The pump unit has a water reservoir 14 on top of the unit and the lower section 15 contains a pump and a driving electric motor. The hand appliance is here shown as a unitary device capable of both toothbrush and water jet operation by simply interchanging the appliance attachments. FIG. 1 shows a toothbrush attachment 16 in place, and FIG. 2 shows a water jet attachment 17 in place.

The hand appliance 11 contains a reciprocating hydraulic piston motor driven by pressure pulses from the pump unit, and a motion converter for producing rotational oscillation of the toothbrush attachment as indicated in FIG. 1(a). The hand appliance also contains an internal conduit for supplying pressure pulses to the water jet attachment shown in FIG. 2. Valve means in the appliance provides for applying the pressure pulses either to the hydraulic motor or to the internal conduit, under the control of a slidable control member 18. In the appliance shown, the forward position of member 18 is for water jet operation, an intermediate position is for toothbrush operation, and the rear position shuts off the appliance.

Suitable constructions are shown in U.S. Pat. Nos. 3,536,065 and 3,771,186, for example.

In FIG. 1 a knob 21 is shown having an Off position, an On-Max. position in which the electric motor is turned on and the pump pressure is maximum, and a MIN. position in which the pump pressure is a minimum. FIGS. 3 and 4 show a combined electric switch and pump pressure regulator in more detail.

Referring to FIG. 3, an hydraulic pump comprises a pump body 22 with an inlet chamber 23 connected to the inlet pipe 24, and a pressure working chamber 25 connected to the outlet pipe 26, and in which the piston 27 is displaced with a longitudinal reciprocating movement. The piston is reciprocated by an electric motor 28 through a suitable motion converter which is generally indicated by dotted line 29.

Mounted in the inlet chamber 23 is the pressure-regulating control member 31 to which is attached the regulating sleeve 32. The central bore 33 of the sleeve serves as a guide for the valve 34. The head of the valve is in the pressure chamber 25 while the stem 35 of the valve and its return spring 36 with retaining ring 37 are in the low-pressure portion of the pump. The end 38 of the control member 31 passes through the wall 39 of the pump housing and is provided with an operating knob 21. The control member 31 is screwed into a threaded insert 41 which is fixed to the end of the pump body 22 by means of a retaining cap 42 of semi-resilient material which clips over the assembly. Ducts 43 are provided in the regulating sleeve 32 to enable the pump to be supplied with liquid from the inlet pipe 24.

The seating 44 in the body of the pump comprises a bore 45 in which there slides the front end of the regulating sleeve 32, which is provided with a plurality of peripherally spaced tapered notches or grooves 46 which decrease in cross-section toward the rear of sleeve 32. The grooves form a bypass and enable the pressure to be regulated in the chamber 25. When the regulating sleeve 32 abuts the shoulder of seating 44, as shown, the chamber pressure is a maximum, and the pressure decreases as the sleeve is moved away from the shoulder. The position of these peripheral grooves 46 is such that for a short travel of the regulating sleeve 32, produced by the rotation of the operating knob 21, the pressure in the chamber 25 remains maximum, which corresponds to the "brushing" position of the device, and upon further travel the pressure is progressively reduced to a minimum pressure.

The pressure regulator is described in more detail in U.S. Pat. No. 3,720,486, to which reference may be made if desired.

The end 38 of the control member 31 is equipped with a radial arm 47 cooperating with the actuating member 48 of an electric switch 49 having a monostable spring-biased member 50 for controlling the electric motor 28. In the position of rest A, the arm 47 bears against member 48 and opens the electric circuit, this position corresponding likewise to the maximum-pressure position of the pump. When the arm 47 is removed from its position of rest by rotation of the operating knob 21, it moves away from member 48 and the switch closes to start the electric motor.

During the small displacement of the regulating sleeve 32, corresponding to the rotation of the operating knob 21 through an angle $\alpha$, the pressure in the chamber 25 remains maximum, because the bypass has not yet been opened. This will be understood from FIG. 3 where the small overlap between sleeve 32 and the adjacent wall of the pump body at point 40 keeps the bypass closed until grooves 46 start to open the bypass to chamber 23.

When the operating knob 21 is turned through an angle greater than the angle $\alpha$, the grooves 46 in the regulating sleeve 32 form a bypass between the chambers 23 and 25, which causes the pressure to drop progressively in the chamber 25 from a maximum pressure down to a minimum pressure when the operating knob sweeps through the angle $\beta$ during its displacement from position B to position C, the regulation of the pressure being used on the one hand when the device serves to feed a spray jet and on the other hand to regulate the power of the brush. Reference marks carried by the operating knob 21 and by the wall 39 of the pump housing indicate the possible different positions of the knob.

With clockwise rotation of knob 21 from its off position, as viewed in FIG. 1, and the knob directly mounted on control member 31, a left-hand thread may be employed on the control member, or a suitable coupling may be employed between knob and control member.

Figure 6:
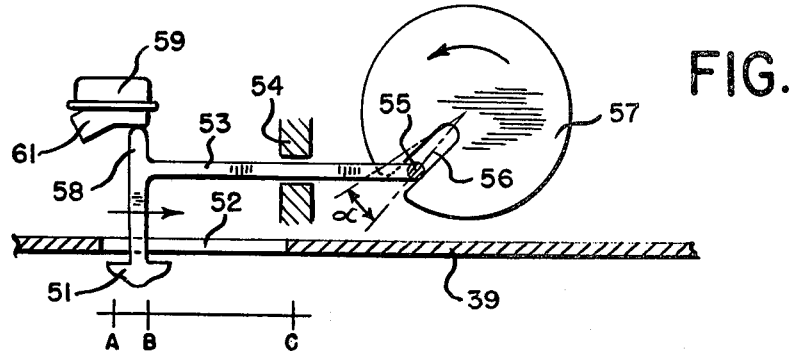
FIG. 6 is a view similar to FIG. 5 but in the going position.

In a modification (FIGS. 5 and 6), the rotary operating knob 21 is replaced by a slider 51 which is displaced along a slot 52 in the wall 39 of the pump casing, between a position A corresponding to the maximum pressure of the pump and a position C corresponding to the minimum pressure. The slider 51 is rigidly connected to a rod 53 moving in a fixed guide 54. Rod 53 cooperates through a connecting member 55 with a radial slot 56 in a rotating disc 57 connected to the control member 31 of the bypass of the pump. The end of the arm 58 of the rod 53 cooperates with a switch 59 having a pivoted actuating member 61 designed for bistable rocking. The open position of the switch (FIG. 5) corresponds to the maximum pressure of the delivery of the pump, which pressure remains constant until the slider reaches the point B (FIG. 6) corresponding to the rotation of the disc 57 through the angle $\alpha$ defined above. Further movement of the slider toward position C gradually decreases the pressure. Here a right-hand thread may be used on the pressure control member to yield the desired movement.

Figure 7:
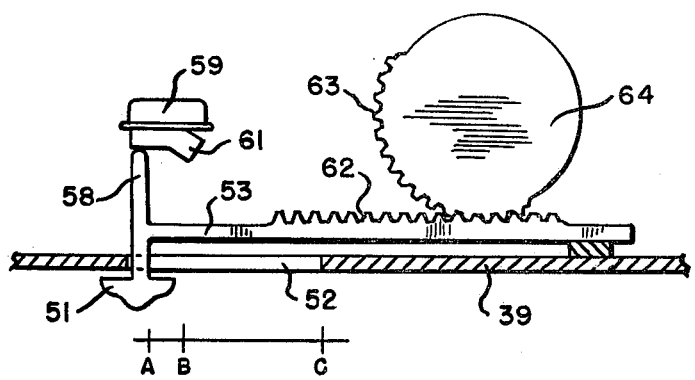
FIG. 7 is a diagrammatic view of a second modified embodiment.

According to another modification (FIG. 7), the connection between the rod 53 of the slider 51 is afforded by a rack 62 which meshes with the teeth 63 of a pinion 64, which is connected to the control member 31 of the pump bypass. In this case, the arm 58 of the rod 53 cooperates as in the previous example with the actuating member 61 of the switch 59.

Figure 8:
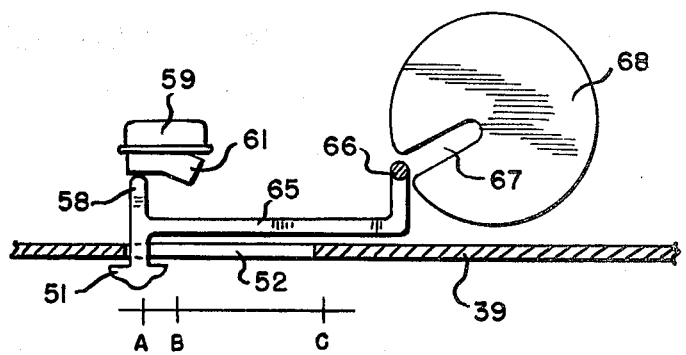
FIG. 8 is a diagrammatic view of a third modified embodiment.

According to a third modification (FIG. 8), the slider 51 is integral with a bent rod 65, the bent end of which is provided with a connecting member 66 which cooperates with the radial slot 67 in a disc 68 connected to the pump bypass control member only after the slider has been displaced from its position A to its position B corresponding to the closing of the switch 59.

The slot 67 may have such a shape that the same result is obtained without its being necessary for the connecting member 66 to leave it.

This form of embodiment is useful if the maximum pressure is only present in the extreme position of the regulating member, for example in the case of a different bypass system.

I claim:
1. In apparatus for body hygiene comprising
   a. an hydraulic pump driven by an electric motor and adapted to produce liquid pressure pulses,
   b. an electric switch for said motor,
   c. and a hand appliance supplied with said liquid pressure pulses and containing an hydraulic motor actuable by said pulses to drive a working attachment, particularly a toothbrush attachment, and means for alternatively supplying said pulses to a liquid jet attachment,
   d. said pump including pressure regulator means for controlling the pressure of said pulses progressively between maximum and minimum values,
   e. a manually actuable control member coupled with said electric switch and pressure regulating means for turning said electric motor on at approximately the position of the regulator means corresponding to maximum pump pulse pressure upon movement of the control member in one direction from the off position thereof and maintaining the motor on upon further movement of the control member toward minimum pump pressure, and for turning the motor off upon movement of the control member in the opposite direction past a position corresponding to approximately maximum pump pulse pressure to said off position.

2. Apparatus according to claim 1 in which, during initial movement of said control member in said one direction to turn the switch on, the pump pulse pressure remains substantially constant at the maximum pressure thereof, the pump pressure decreasing upon further movement of the control member in said one direction.

3. Apparatus according to claim 1 in which said control member is connected to actuate said pressure regulator means between two extreme positions, and said pressure regulator means includes bypass means which is closed in one extreme position and progressively opens as the control member is moved toward the other extreme position.

4. Apparatus according to claim 1 in which said switch is spring-biased toward its closed position, and said coupling includes switch actuating means for holding the switch open when said control member is in its "off" position and allowing the switch to open upon movement of the control member in said one direction.

5. Apparatus according to claim 1 in which said pressure regulator means is rotatable and said control member is a slider mounted for translational displacement, and including a rack on said slider and a cooperating pinion attached to the rotatable pressure regulator means, said slider including means for actuating said switch.

6. Apparatus according to claim 1 in which said switch is bistable.

7. Apparatus according to claim 4 in which said pressure regulator means is rotatable and said control member is a knob connected thereto, and said switch actuating means is connected to the rotatable pressure regulator means.

8. Apparatus according to claim 1 in which said control member is a slider mounted for translational displacement and said pressure regulator means is rotatable, and including a radially-slotted disk attached to the rotatable pressure regulator means, said slider including means for actuating said switch and means engageable in the slot of said disc to rotate the disk.

9. Apparatus according to claim 8 in which said slotted disk and the means on the slider engageable therewith are designed and adapted to produce rotation of the disk after an initial movement of the slider which closes said switch.

* * * * *